US009681818B2

(12) United States Patent
Govari et al.

(10) Patent No.: US 9,681,818 B2
(45) Date of Patent: Jun. 20, 2017

(54) DETECTION AND DISPLAY OF IRREGULAR PERIODIC WAVEFORMS

(71) Applicant: BIOSENSE WEBSTER (ISRAEL) LTD., Yokneam (IL)

(72) Inventors: Assaf Govari, Haifa (IL); Yaron Ephrath, Karkur (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 80 days.

(21) Appl. No.: 14/571,708

(22) Filed: Dec. 16, 2014

(65) Prior Publication Data

US 2016/0166165 A1    Jun. 16, 2016

(51) Int. Cl.
| | |
|---|---|
| G08C 19/22 | (2006.01) |
| A61B 5/044 | (2006.01) |
| A61B 5/0456 | (2006.01) |
| A61B 5/04 | (2006.01) |
| A61B 5/0452 | (2006.01) |
| A61B 5/00 | (2006.01) |
| A61B 5/042 | (2006.01) |
| G09G 5/00 | (2006.01) |

(52) U.S. Cl.
CPC .......... *A61B 5/044* (2013.01); *A61B 5/04012* (2013.01); *A61B 5/0456* (2013.01); *A61B 5/04525* (2013.01); *A61B 5/7475* (2013.01); *A61B 5/0422* (2013.01); *A61B 5/6852* (2013.01); *G09G 5/00* (2013.01); *G09G 2340/14* (2013.01)

(58) Field of Classification Search
CPC . A61B 5/044; A61B 5/04012; A61B 5/04524; A61B 5/04525; A61B 5/7475
USPC ............................................ 340/870.07, 870.03
See application file for complete search history.

(56) References Cited

U.S. PATENT DOCUMENTS 3,457,452 A * 7/1969 Saper .................. A61B 5/044
315/364
3,638,066 A    1/1972 Paine et al.
(Continued)

FOREIGN PATENT DOCUMENTS

| EP | 2030565 A1 | 3/2009 |
|---|---|---|
| WO | 2006123334 A2 | 11/2006 |
| WO | WO 2010/054409 A1 | 5/2010 |

OTHER PUBLICATIONS

European Search Report for corresponding European Application No. EP15200052 dated Apr. 28, 2016.

*Primary Examiner* — Qutbuddin Ghulamali
(74) *Attorney, Agent, or Firm* — Notaro, Michalos & Zaccaria P.C.

(57) ABSTRACT

A method for display, consisting of acquiring an electrical signal from a heart of a subject over multiple heart cycles. The electrical signal is partitioned into a succession of synchronized segments having respective start times at a selected annotation point in the heart cycles. The method includes overlaying respective graphical representations of the synchronized segments in the succession on a display screen, such that each segment is first presented on the display screen with an initial display intensity at a respective display time corresponding to a respective start time of the segment. The method further includes gradually decreasing a display intensity of each segment overlaid on the display screen as a decaying function of a time elapsed since the respective display time.

18 Claims, 5 Drawing Sheets

(56) References Cited

U.S. PATENT DOCUMENTS

| | | | |
|---|---|---|---|
| 5,284,152 A * | 2/1994 | Portnuff | G06F 19/3406 600/525 |
| 7,502,643 B2 * | 3/2009 | Farringdon | A61B 5/0428 600/509 |
| 2002/0091330 A1 | 7/2002 | MacAdam et al. | |
| 2004/0030257 A1 | 2/2004 | Tabbara et al. | |
| 2005/0190830 A1 * | 9/2005 | Miyashita | H04L 1/24 375/228 |
| 2007/0208260 A1 | 9/2007 | Afonso | |
| 2011/0130671 A1 * | 6/2011 | MacQuarrie | A61B 5/02 600/513 |
| 2012/0204875 A1 | 8/2012 | Brazy et al. | |
| 2013/0245476 A1 | 9/2013 | Takizawa et al. | |

\* cited by examiner

DETECTION AND DISPLAY OF IRREGULAR PERIODIC WAVEFORMS

FIELD OF THE INVENTION

The present invention relates generally to displays of a signal, and specifically to displays of an irregular, periodic signal.

BACKGROUND OF THE INVENTION

During a cardiac procedure, the condition of the heart may be monitored, inter alia, by observing electrophysiological data in a graphical form, typically as potential vs. time graphs. While the heart is in a sinus condition, the periodic electrocardiogram (ECG) waveforms generated by the heart are relatively uncomplicated. However, in some non-sinus conditions of the heart, such as during atrial fibrillation, each periodic ECG signal may include one or more features that may only occur in some of the periodic signals, but not in every signal. Because of the irregularity of the signals, it is difficult to distinguish these features.

PCT Application WO 2010/054409, to Ramanathan et al., whose disclosure is incorporated herein by reference, describes a method for visualization of electrophysiology data. Electroanatomic data representing electrical activity on a surface of an organ over a time period is stored. An interval within the time period is selected in response to a user selection. Responsive to the user selection of the interval, a visual representation of physiological information for the user selected interval is generated by applying at least one method to the electroanatomic data. The visual representation is spatially represented on a graphical representation of a predetermined region of the surface of the organ.

U.S. Patent Application 2013/0245476, to Takizawa et al., whose disclosure is incorporated herein by reference, describes a cardiac muscle excitation waveform detector. The detector includes a waveform acquisition section that acquires, in a preset period, a waveform from an intracardiac electrocardiogram measured in the middle of occurrence of atrial fibrillation. The disclosure is stated to show a result of a mean conduction time that is calculated under an analysis technique described in the disclosure.

U.S. Patent Application 2007/0208260, to Afonso, whose disclosure is incorporated herein by reference, describes a system for presenting information representative of patient electrophysiological activity, such as complex fractionated electrogram information. The disclosure describes a presentation device that presents electrogram information as associated with a location at which it was measured on a model of the patient's heart.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method for display, including:

acquiring an electrical signal from a heart of a subject over multiple heart cycles;

partitioning the signal into a succession of synchronized segments having respective start times at a selected annotation point in the heart cycles;

overlaying respective graphical representations of the synchronized segments in the succession on a display screen, such that each segment is first presented on the display screen with an initial display intensity at a respective display time corresponding to a respective start time of the segment; and gradually decreasing a display intensity of each segment overlaid on the display screen as a decaying function of a time elapsed since the respective display time.

Typically, overlaying the respective graphical representations includes summing the display intensity of the synchronized segments at overlapping points of the synchronized segments. Summing the display intensity may include summing the display intensity for a selected portion of the synchronized segments, wherein the selected portion is smaller than the synchronized segments.

In a disclosed embodiment overlaying the respective graphical representations includes summing the display intensity of the synchronized segments at points, of the synchronized segments, within a selected number of pixels of the display screen from each other.

In a further disclosed embodiment the selected annotation point is derived from a QRS complex of the heart signal.

In a yet further disclosed embodiment overlaying the respective graphical representations includes aligning respective baselines of the synchronized segments.

In an alternative embodiment overlaying the respective graphical representations includes aligning the selected annotation point of each of the synchronized segments with one another.

There is further provided, according to an embodiment of the present invention, apparatus, including:

a display screen; and a processor, which is configured to:

acquire an electrical signal from a heart of a subject over multiple heart cycles, partition the signal into a succession of synchronized segments having respective start times at a selected annotation point in the heart cycles, overlay respective graphical representations of the synchronized segments in the succession on the display screen, such that each segment is first presented on the display screen with an initial display intensity at a respective display time corresponding to a respective start time of the segment, and gradually decrease a display intensity of each segment overlaid on the display screen as a decaying function of a time elapsed since the respective display time.

The present disclosure will be more fully understood from the following detailed description of the embodiments thereof, taken together with the drawings, in which:

DETAILED DESCRIPTION OF EMBODIMENTS

Overview

In certain conditions of the heart, such as some types of atrial fibrillation, each periodic ECG (electrocardiogram) signal may include one or more waveform features that only occur in some of the signals, but not in every signal. These irregularly recurring waveforms are periodic, in the sense that when they do recur, the recurrence is at approximately the same position (in time) in the signal. Because of the irregularity, the waveforms are difficult to distinguish.

Embodiments of the present invention provide a method for viewing the ECG signals so that the irregularly recurring waveforms are made more visible. A set of signals is acquired from the heart of a subject, the set being taken over multiple heart cycles of the subject. A processor partitions the signals into a succession of synchronized segments, using a common annotation point as a start time for each of the segments. A typical segment uses a part of the QRS complex of the ECG signal as the start time, and the succeeding QRS complex as the end time, to define the segments.

Graphical representations of the synchronized segments are overlaid on each other on a display screen, using the common annotation point as a registration point for the segments. The overlaid segments may also be overlaid on each other so that their baselines are aligned. The segments are presented on the display screen at a respective display time corresponding to a respective start time of the segment. In addition each segment is displayed with a common initial display intensity, and the display intensity of each segment is decreased as a decaying function of time elapsed since the initial presentation of the segment on the display screen. There are thus typically a number of different signals with different intensities on the display screen.

Where points or regions of the segments overlap, the display intensities of the overlapping points are summed. The summing emphasizes the irregularly recurring waveforms in the signals, making the waveforms significantly more visible than in prior art signal displays.

System Description

Figure 1:
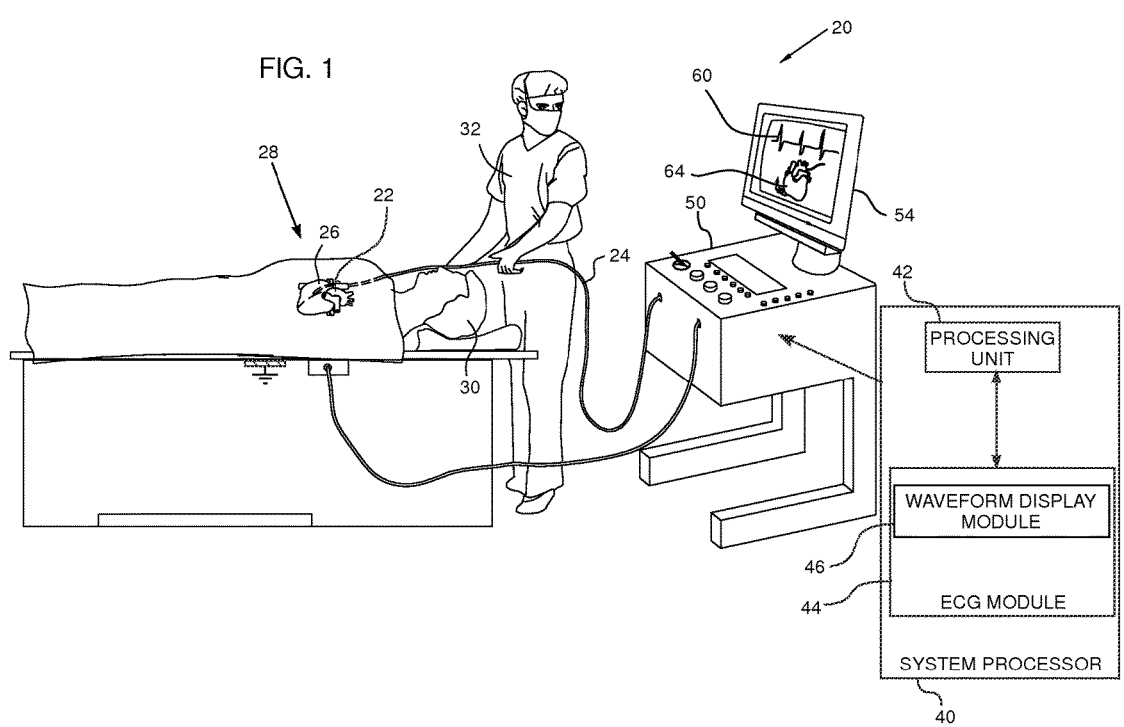
FIG. 1 is a schematic illustration of a waveform display system, according to an embodiment of the present invention.

Reference is now made to FIG. 1, which is a schematic illustration of a waveform display system 20, according to an embodiment of the present invention. System 20 is typically used during a medical procedure on a body organ, and in the description herein the body organ, by way of example, is assumed to comprise the heart, wherein the system is applied to display electrocardiogram (ECG) signals. Typically the system is used when the heart is undergoing atrial fibrillation, and the ECG signals may be intra-cardiac signals or signals derived from a location external to the heart, such as from a patient's skin. However, it will be understood that system 20 may be used for other states of the heart, including a sinus rhythm state, or for other signals, such as electroencephalograph (EEG) signals.

For clarity, except where otherwise stated, in the following description the signals displayed by system 20 are assumed to be ECG signals.

The description herein assumes that system 20 senses intra-cardiac ECG signals from a heart 22, using a probe 24. A distal end 26 of the probe is assumed to have an electrode 28 for sensing the signals. Typically, probe 24 comprises a catheter which is inserted into the body of a subject 30 during a cardiac procedure performed by a user 32 of system 20. In the description herein user 32 is assumed to be a medical professional.

System 20 may be controlled by a system processor 40, comprising a processing unit 42 communicating with an ECG module 44. Module 44 in turn comprises a waveform display module 46. Processor 40 may be mounted in a console 50, which comprises operating controls which typically include a pointing device such as a mouse or trackball. Professional 32 uses the pointing device to interact with the processor, which, as described below, may be used to present results produced by system 20 to the professional on a display screen 54.

Figure 2:
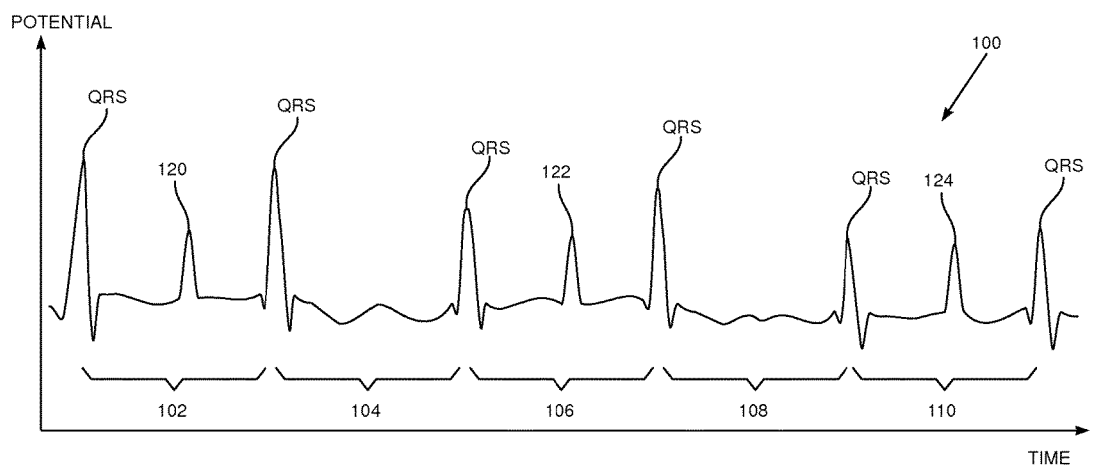
FIG. 2 is a schematic potential vs. time graph of an ECG signal derived from a heart, according to an embodiment of the present invention.

The screen displays results of analysis and processing of ECG signals by ECG module 44. Typically, the resultant ECG signals are presented on screen 54 in the form of a potential vs. time graph, and a schematic example 60 of such a graph is illustrated in FIG. 1. (A more detailed graph is shown in FIG. 2, described below.) However, the resultant ECG signals may also be used by processor 40 to derive other results associated with the ECG signals, such as a local activation time (LAT). These results are typically presented on screen 54 in the form of a three-dimensional (3D) map 64 of the internal surface of heart 22.

Processor 40 uses software stored in a memory of the processor to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 typically comprises other modules, such as a probe tracking module, a force module that measures a force on distal end 26, and an ablation module that provides regulated to power to electrode 28, or another electrode in the distal end. For simplicity, such modules are not shown in FIG. 1. The Carto® system produced by Biosense Webster, of Diamond Bar, Calif., uses such modules.

FIG. 2 is a schematic potential vs. time graph 100 of an ECG signal derived from heart 22, according to an embodiment of the present invention. By way of example, graph 100 illustrates six QRS complexes occurring in the ECG signal, the complexes repeating at substantially regular intervals, and dividing the signal into five segments 102, 104, 106, 108, and 110. A heart beating in sinus rhythm, i.e., a "normal" heart, generates ECG signals that, except for minor variations between successive QRS complexes, comprise regular repeating substantially invariant segments. However, while graph 100 is periodic, having repeating QRS complexes, successive segments are irregular. Thus segments 102, 106, and 110 have respective peaks 120, 122, and 124 in the segments, whereas segments 104 and 108 have no such peaks. Such an irregular yet periodic waveform is typical of signals produced during some types of atrial fibrillation.

Figure 3:
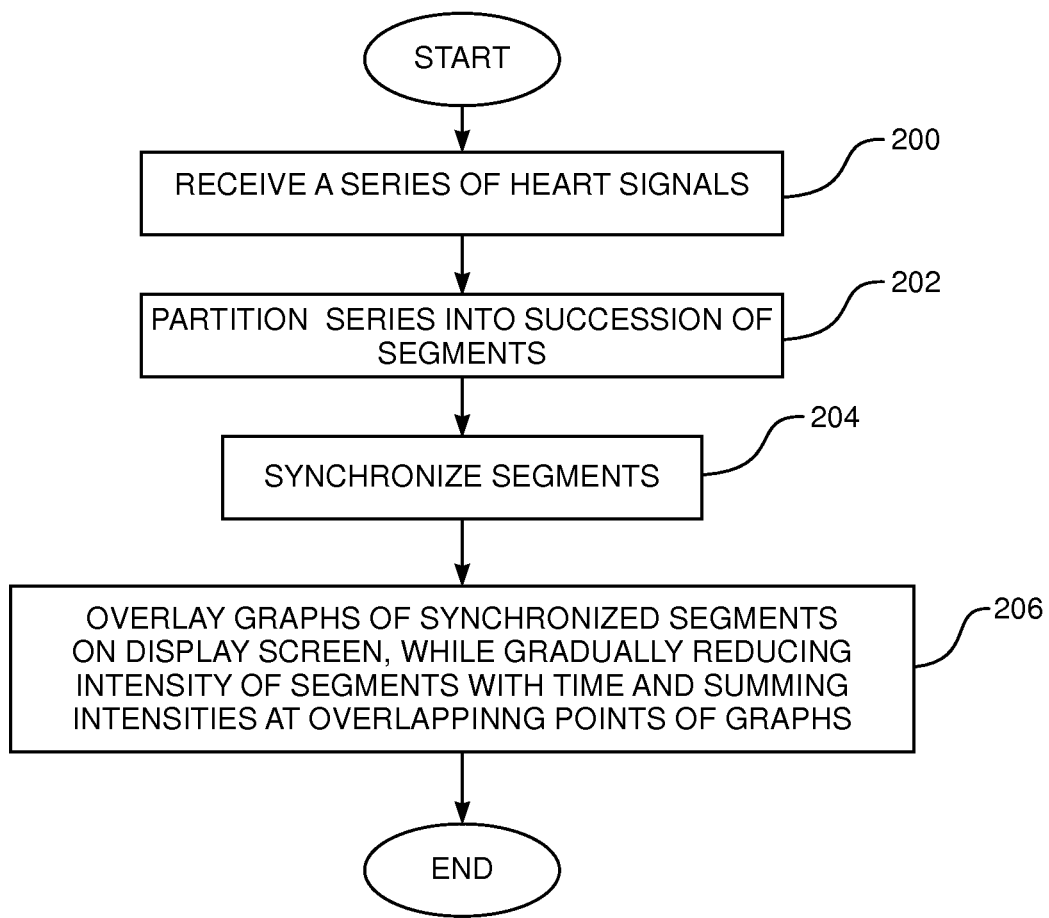
FIG. 3 is a flowchart of steps performed in implementing the waveform display system, according to an embodiment of the present invention.
Figure 4:
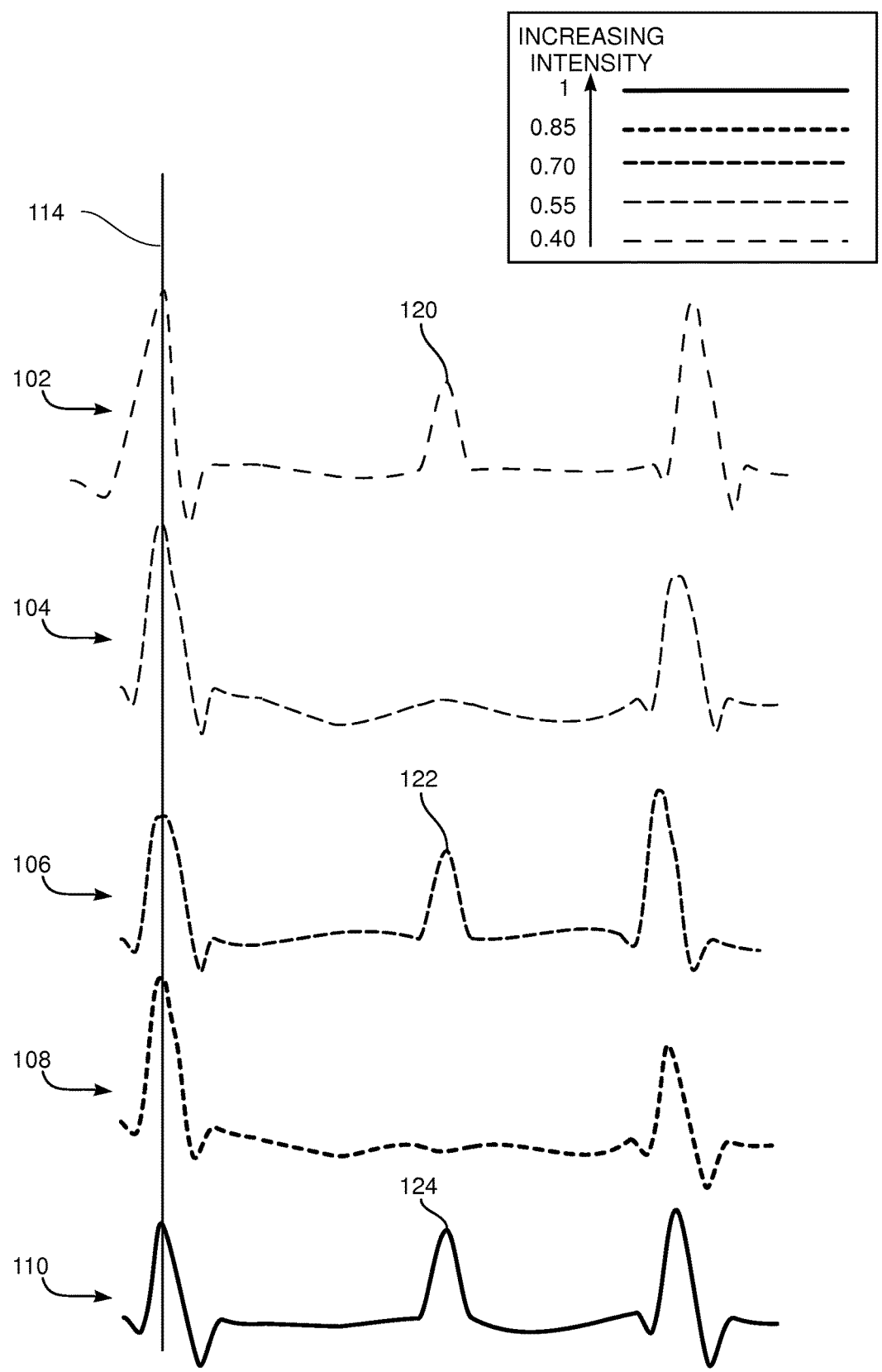
FIG. 4 shows schematic graphs illustrating some of the actions executed in the steps of the flowchart, according to an embodiment of the present invention.

FIG. 3 is a flowchart of steps performed by processor 40, together with modules 44 and 46, in implementing system 20, and FIG. 4 shows schematic graphs illustrating some of the actions executed in the steps, according to embodiments of the present invention. FIG. 2 is also used to illustrate some of the actions of the flowchart steps.

In an initial step 200, processor 40 receives a series of heart signals, such as is illustrated by graph 100.

In a partition step 202, the processor partitions the series into a succession of segments, using a selected annotation point as a fiducial start time for each of the segments. Typically, the annotation point is derived from the signal received by electrode 28. Alternatively, the annotation point is derived from another ECG signal, which may be acquired by another electrode on the catheter, or alternatively as a body surface signal from a body surface electrode. By way of example, the selected annotation points for the segments of graph 100 are assumed to be the peak of the QRS complex, and each segment is assumed to terminate at the next successive QRS complex. The succession of segments 102, 104, 106, 108, and 110, after they have been partitioned, is illustrated in FIG. 4.

In a synchronization step 204, the succession of segments is synchronized to the selected annotation point. The synchronization is illustrated in FIG. 4 by the peaks of the initial QRS complex of each segment being located on a vertical line 114.

In a display step 206 graphs of the successive synchronized segments are presented on display screen 54, the segments being aligned and overlaid with each other according to the selected annotation point. In some embodiments professional 32 selects the signal (different possible signals are described above in step 202) to be used for the selected annotation point, typically by preliminary observation of sets of overlaid segments, so as to determine the signal giving the most stable synchronization. Typically the alignment also includes aligning an estimated baseline of each segment. Each segment is first presented with an initial display intensity at a display time corresponding to the start time of the segment.

After initial presentation, the display intensity of each segment is allowed to decay, according to a predetermined decay function of a time elapsed since the initial presentation. A typical decay function reduces the intensity linearly by 15% for the time period between adjacent segments, so that after seven time periods, the display intensity is zero, i.e., the segment is not displayed. However, any other convenient function may be used for the reduced intensity.

FIG. 4 illustrates the different display intensities of the five segments of graph 100, according to the presentation times of the segments shown in FIG. 2. Thus, in FIG. 2, the most recent segment is segment 110, and the elapsed time from presentation of each of the segments, compared to the presentation time for segment 110, increases monotonically through segments 108, 106, 104, and 102, so that segment 102 has the largest elapsed time. For clarity, FIG. 4 shows the different segments as being separated vertically. Since the elapsed times for the respective segments 108, 106, 104, and 102 increases, the display intensities of the segments decreases. By way of example, assuming the linear intensity reduction of 15% described above, and an intensity if 1 (measured in arbitrary units) for segment 110, segments 108, 106, 104, and 102 have respective intensities of 0.85, 0.7, 0.55, and 0.4.

Figure 5:
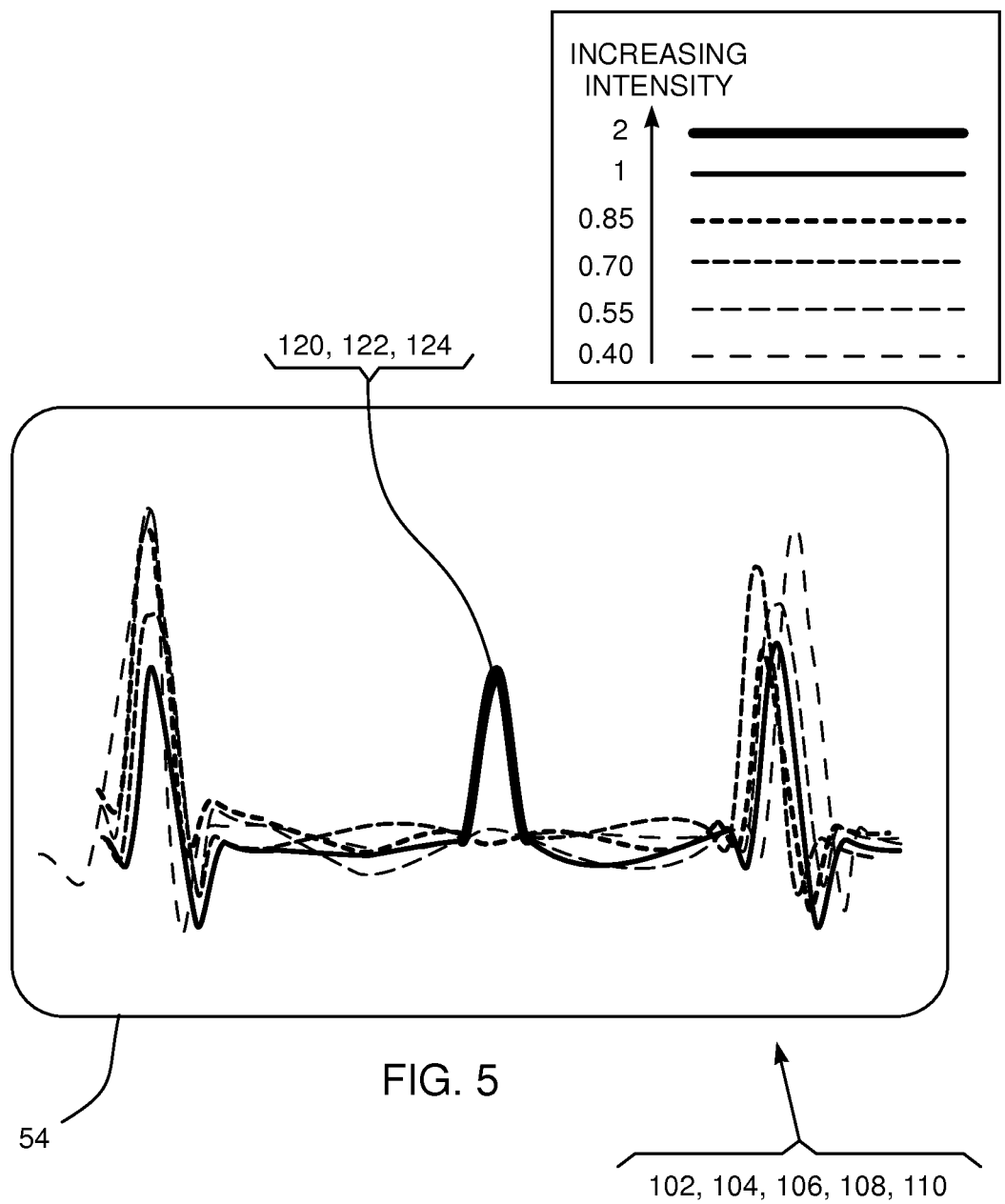
FIG. 5 illustrates different segments of a waveform as they are overlaid on a display screen, according to an embodiment of the present invention.

FIG. 5 illustrates the different segments as they are overlaid on display screen 54, according to an embodiment of the present invention. As the segments are overlaid, processor 40 sums the intensities of overlapping points of the graph. The summing enhances the visibility of regions of the graphs that repeat on an irregular basis. Thus, as illustrated, in overlaid segments 102, 104, 106, 108, and 110 peaks 120, 122, and 124 overlap, so that the intensity of the overlapped points is increased compared to the intensity of non-overlapped sections of the graphs. As shown in FIG. 4, peaks 120, 122, and 124 have respective intensities 0.4, 0.7, and 1, so that the overlapped peaks have a nominal intensity of 2.1. FIG. 5 illustrates the overlapped peaks as having an intensity on screen 54 of 2.

The embodiments described above have assumed that each segment is assigned an intensity according to the time elapsed on the display screen since its first presentment on the screen, and that where the segments overlap the intensities are summed. In an alternative embodiment of the present invention, rather than the intensity summation being applied to complete segments, the intensity summation is only applied to a portion of each of the segments. Typically, the portion to which the summation applies is selected by professional 32.

For example, the professional may choose that the summation is only applied to the central 75% of each segment. This type of limitation allows system 20 to only enhance, by increasing their intensity, selected sections of the segments that are of interest to the professional, while not enhancing other sections, such as the start QRS complex and/or the end QRS complex, of the segments.

In a further alternative embodiment, rather than summing the intensities where segments overlap, e.g., where two or more segments have portions occupying the same pixels on screen 54, the intensities may be configured to be summed if two or more segments have portions occupying pixels that are close to each other. The degree of closeness may be selected by professional 32, and may be, for example where portions are within a selected number, for example 2, of pixels of each other. Allowing this type of summation provides the professional with the ability to sum sections that are of interest, even if there are slight variations, typically due to noise, between the sections of interest. The result of the summation may be presented on screen 54 as one or more pixels, with the summed intensity, at a mean location of the pixels that are close to each other.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for diagnosing atrial fibrillation in a subject, comprising:
   acquiring an electrocardiogram (ECG) signal from a heart of the subject over multiple heart cycles;
   partitioning the ECG signal into a succession of synchronized segments each having respective start times at a selected annotation point in the respective heart cycles, wherein said synchronized segments each represent heart cycles occurring at different time points;
   providing a display screen having a display axis, the display axis representing a time period corresponding to one synchronized segment;
   simultaneously displaying graphical representations of a plurality of synchronized segments on the display axis, such that synchronized segments corresponding to ECG signals from a plurality of different heart cycles occurring at different time points are simultaneously overlaid on the display axis, and wherein said graphical representations of the plurality of synchronized segments at least partially overlap on the display screen;
wherein additional synchronized segments are continuously created as the ECG signal is received from the heart of the subject, wherein graphical representations of newly created synchronized signals are continuously added to the display axis on the display screen, and wherein graphical representations of older synchronized signals are removed from the display axis after a period of time;
wherein each synchronized segment is first presented on the display screen with an initial display intensity at a respective display time corresponding to a respective start time of the synchronized segment;
gradually decreasing a display intensity of the graphical representation of each synchronized segment overlaid on the display screen as a decaying function of a time elapsed since the respective display time until each synchronized segment is, in respective turn, removed from the display axis; and
wherein graphical representations of synchronized segments having a plurality of different respective display intensities are simultaneously presented on the display axis;
the method further comprising:
determining whether said plurality of graphical representations of the plurality of synchronized segments on the display axis comprise both (i) one or more synchronized segments which each include an irregular but periodic wave form, and also (ii) one or more synchronized segments which do not include said irregular but periodic wave form; and
diagnosing atrial fibrillation in the subject when condition (i) and (ii) are both satisfied.

2. The method according to claim 1,
wherein where said graphical representations of said synchronized segments overlap on the display axis, the display intensity of overlapping points of the synchronized segments are summed and displayed on the display screen.

3. The method according to claim 2, wherein summing the display intensity comprises summing the display intensity for a selected portion of the synchronized segments, and wherein the selected portion is smaller than the synchronized segments.

4. The method according to claim 1,
wherein where portions of said graphical representations of said synchronized segments are within a selected number of pixels from each other on the display axis, the display intensity of said portions of the synchronized segments are summed and displayed on the display screen.

5. The method according to claim 1, wherein the selected annotation point is derived from a QRS complex of the heart signal.

6. The method according to claim 1, wherein overlaying the respective graphical representations comprises aligning respective baselines of the synchronized segments.

7. The method according to claim 1, wherein overlaying the respective graphical representations comprises aligning the selected annotation point of each of the synchronized segments with one another.

8. The method of claim 1, the method further comprising:
determining whether said plurality of graphical representations of the plurality of synchronized segments on the display axis comprise both (i) a plurality of synchronized segments which each include an irregular but periodic wave form, and also (ii) one or more synchronized segments which do not include said irregular but periodic wave form;
the method comprising diagnosing atrial fibrillation in the subject when condition (i) and (ii) are both satisfied; and
wherein said (i) plurality of synchronized segments which each include said irregular but periodic wave form are at least partially represented on the display screen by a summed intensity of overlapping points corresponding to the irregular but periodic wave form in two or more different synchronized segments.

9. The method according to claim 1, wherein each synchronized segment corresponds to one heart cycle.

10. Apparatus, comprising:
a display screen; and
a processor, which is configured to:
acquire an electrocardiogram (ECG) signal from a heart of a subject over multiple heart cycles;
partition the ECG signal into a succession of synchronized segments each having respective start times at a selected annotation point in the respective heart cycles, wherein said synchronized segments each represent ECG signals from heart cycles occurring at different time points;
provide a display axis on the display screen, the display axis representing a time period corresponding to one synchronized segment;
simultaneously display graphical representations of a plurality of synchronized segments on the display axis, such that synchronized segments corresponding to ECG signals from a plurality of different heart cycles occurring at different time points are simultaneously overlaid on the display axis, and wherein said graphical representations of the plurality of synchronized segments at least partially overlap on the display screen;
continuously create additional synchronized segments as the ECG signal is received from the heart of the subject, wherein graphical representations of newly created synchronized signals are continuously added to the display axis on the display screen, and wherein graphical representations of older synchronized signals are removed from the display axis after a period of time;
first present each synchronized segment on the display screen with an initial display intensity at a respective display time corresponding to a respective start time of the synchronized segment; and
gradually decrease a display intensity of the graphical representation of each synchronized segment overlaid on the display screen as a decaying function of a time elapsed since the respective display time until each synchronized segment is, in respective turn, removed from the display axis; and
wherein graphical representations of synchronized segments having a plurality of different respective display intensities are simultaneously presented on the display axis;
said processor being further configured to:
determine whether said plurality of graphical representations of the plurality of synchronized segments on the display axis comprise both (i) one or more synchronized segments which each include an irregular but periodic wave form, and also (ii) one or more synchronized segments which do not include said irregular but periodic wave form; and
to indicate atrial fibrillation in the subject when condition (i) and (ii) are both satisfied.

11. The apparatus according to claim 10,
said processor being configured so that where said graphical representations of said synchronized segments overlap on the display axis, the display intensity of overlapping points of the synchronized segments are summed and displayed on the display screen.

12. The apparatus according to claim 11, wherein summing the display intensity comprises summing the display intensity for a selected portion of the synchronized segments, and wherein the selected portion is smaller than the synchronized segments.

13. The apparatus according to claim 10,
said processor being configured so that where portions of said graphical representations of said synchronized segments are within a selected number of pixels from each other on the display axis, the display intensity of said portions of the synchronized segments are summed and displayed on the display screen.

14. The apparatus according to claim 10, wherein the selected annotation point is derived from a QRS complex of the heart signal.

15. The apparatus according to claim 10, wherein overlaying the respective graphical representations comprises aligning respective baselines of the synchronized segments.

16. The apparatus according to claim 10, wherein overlaying the respective graphical representations comprises aligning the selected annotation point of each of the synchronized segments with one another.

17. A method for diagnosing atrial fibrillation in a subject, comprising:
acquiring an electrical signal from a heart of the subject over multiple heart cycles;
partitioning the signal into a succession of synchronized segments each having respective start times at a selected annotation point in the respective heart cycles, wherein said synchronized segments each represent signals from one heart cycle of said subject, said synchronized signals each representing respective heart cycles occurring at different time points;
providing a display screen having a display axis, the display axis representing a time period corresponding to both one heart cycle of the subject, and to one synchronized segment;
simultaneously displaying graphical representations of a plurality of synchronized segments on the display axis, such that synchronized segments corresponding to signals from a plurality of different heart cycles occurring at different time points are simultaneously overlaid on the display axis, and wherein said graphical representations of the plurality of synchronized segments at least partially overlap on the display screen; and
wherein additional synchronized segments are continuously created as the signal is received from the heart of the subject, wherein graphical representations of newly created synchronized signals are continuously added to the display axis on the display screen, and wherein graphical representations of older synchronized signals are removed from the display axis after a period of time; and
the method further comprising:
determining whether said plurality of graphical representations of the plurality of synchronized segments on the display axis comprise both (i) one or more synchronized segments which each include an irregular but periodic wave form, and also (ii) one or more synchronized segments which do not include said irregular but periodic wave form; and
diagnosing atrial fibrillation in the subject when condition (i) and (ii) are both satisfied.

18. The method of claim 17, further comprising:
gradually decreasing a display intensity of the graphical representation of each synchronized segment overlaid on the display screen until each synchronized segment is, in respective turn, removed from the display axis, and
wherein graphical representations of synchronized segments having a plurality of different respective display intensities are simultaneously presented on the display axis.

* * * * *